United States Patent
Pryce-Lewis et al.

(10) Patent No.: US 7,521,254 B2
(45) Date of Patent: Apr. 21, 2009

(54) QUANTITATIVE MEASUREMENTS OF CONCENTRATION AND SOLUBILITY USING RAMAN SPECTROSCOPY

(75) Inventors: Wendy Pryce-Lewis, Lexington, MA (US); Evie Sun, Cambridge, MA (US); Kentaro Shimizu, San Mateo, CA (US)

(73) Assignee: Transform Pharmaceuticals, Inc., Lexington, MA (US)

( * ) Notice: Subject to any disclaimer, the term of this patent is extended or adjusted under 35 U.S.C. 154(b) by 912 days.

(21) Appl. No.: 11/103,239

(22) Filed: Apr. 11, 2005

(65) Prior Publication Data
US 2005/0228594 A1  Oct. 13, 2005

Related U.S. Application Data

(60) Provisional application No. 60/561,386, filed on Apr. 12, 2004.

(51) Int. Cl.
*G01N 21/65* (2006.01)
*G01J 3/44* (2006.01)

(52) U.S. Cl. .................... 436/171; 356/301; 436/4; 436/183; 702/25

(58) Field of Classification Search .......... 356/301; 436/4, 171, 183; 702/22, 25
See application file for complete search history.

(56) References Cited

U.S. PATENT DOCUMENTS

| | | | |
|---|---|---|---|
| 4,620,284 A | 10/1986 | Schnell et al. | |
| 5,481,113 A | 1/1996 | Dou et al. | |
| 5,553,616 A | 9/1996 | Ham et al. | |
| 5,652,653 A | 7/1997 | Alsmeyer et al. | |
| 6,313,914 B1 | 11/2001 | Roe | |
| 2003/0059837 A1 | 3/2003 | Levinson et al. | |
| 2003/0124028 A1* | 7/2003 | Carlson et al. ............. | 422/68.1 |
| 2003/0138940 A1 | 7/2003 | Lemmo et al. | |

FOREIGN PATENT DOCUMENTS

| WO | 01059437 | 8/2001 |
|---|---|---|
| WO | 03016883 | 3/2007 |

OTHER PUBLICATIONS

Jones, D. S. et al, Journal of Pharmaceutical Sciences 2000, 89, 563-571.*
Stowell, G. W. et al, Journal of Pharmaceutical Sciences 2002, 91, 2481-2488.*
Savolainen, M. et al, International Journal of Pharmaceutics 2003, 262, 47-62.*
Anquetil et al., "Laser Raman Spectroscopic Analysis of Polymorphic Forms in Microliter Fluid Volumes", Journal of Pharmaceutical Sciences, vol. 92, No. 1, Jan. 2003, pp. 149-160.
Hubschmid, et al., Laser Spectroscopy in Combustion Research, "Application of Raman spectroscopy: Species concentration and temperature measurements for catalytically stabilized combustion", ERCOFTAC Summer School, Mar. 2002, Zurich, pp. 3-1 to 318.

* cited by examiner

*Primary Examiner*—Arlen Soderquist

(57) ABSTRACT

The present invention provides methods which allows for the determination of concentration or solubility in a multi-component system using Raman spectroscopy. The present invention circumvents the necessity of constructing a calibration curve in order to analytically determine the concentration/solubility of a solute in a homogeneous liquid or a homogeneous solid. Methods of determining the saturation concentration of a solute in a polymer matrix or a polymer matrix film are also provided.

2 Claims, 12 Drawing Sheets

QUANTITATIVE MEASUREMENTS OF CONCENTRATION AND SOLUBILITY USING RAMAN SPECTROSCOPY

CROSS-REFERENCE TO RELATED APPLICATION

The present application claims the benefit of priority of U.S. Provisional Application Ser. No. 60/561,386, filed Apr. 12, 2004 which is hereby incorporated by reference herein in its entirety, including any figures, tables or drawings.

FIELD OF THE INVENTION

The present invention relates to the concentration and solubility measurements of a solute in polymeric and multi-component systems.

BACKGROUND OF THE INVENTION

In technical fields relating to chemical formulation of compounds, such as, but not limited to the fields of pharmaceutical and agrochemical research and development, it is frequently necessary to evaluate the general suitability of a newly developed active pharmaceutical ingredient (API) candidate prior to launching into full development. Such an evaluation of the general suitability or, in the field of pharmaceutical development, therapeutic effectiveness of such chemical compounds typically includes solubility studies of the compound in various solvents as well as solubility profiles at various pH values.

However, carrying out such studies for a great many compounds can be problematic and resource-intensive. At the earlier stages of the drug discovery process, in particular, the solubility measurements are generally performed for a large variety of compounds. Furthermore, many of these compounds are only available in limited quantities, either due to difficulties in manufacturing larger quantities or simply because the cost of producing or handling larger quantities of the compounds is not feasible.

However, simply bypassing the solubility studies is also not a viable option for product development as selection of an otherwise suitable candidate compound that does not have a suitable solubility profile can cause significant problems. Indeed, insoluble or poorly soluble compounds often prove difficult to develop into drugs. Even with significant motivation, the development of low-solubility drugs is more time-consuming and expensive than for a compound with otherwise more suitable properties. Traditionally, "equilibrium" solubility has been determined by agitating or shaking the compound with the solvent of choice for at least 24 hours or until no more of the compound will dissolve, then filtering, and determining the concentration of dissolved compound by a suitable analytical assay. These analytical assays have to be calibrated, a process which includes preparation of at least several solutions of known varied concentrations of the compound (standard solutions), and establishing a quantitative relationship between a measurable analytical signal and the compound concentration. This approach is inappropriate in a modern drug discovery setting. The throughput, or number of unknown samples that can be determined in a given amount of time, and using a given quantity of resources, such as machines, personnel, samples, and the like, is insufficient to meet the required demand to analyze a great number of potential lead compounds. For example, determination of the mass of samples and/or standards presents too restrictive a checkpoint in the process for maintaining the high throughput desired as the process demands weighing hundreds (or thousands) of solid samples in submilligram quantities.

The present invention provides new methods for the measurement of concentration and solubility of an API in a multi-component system without the need of preparing a plurality of standard samples with a distribution of well-defined concentrations or the generation of a traditional calibration curve.

The present invention also provides methods of determining the saturation concentration ($C_{sat}$) of a solute in a polymer matrix or a polymer matrix film. In order to find the saturation concentration of a solute in a polymer network, it is often necessary to titrate a series of formulations and then to wait for long periods of time for the solute in supersaturated systems to diffuse, form a critical nucleus and grow. The formulations are visually observed after a given period and the solubility is estimated. This method can lead to over-estimated solubility limits since it can take weeks, months, or years before crystallization occurs in some systems. The induction time depends on factors such as the glass transition temperature of the polymer, the size of the permeant, the temperature, and the concentration driving force. In a titration series, the formulations closest to, but still above, the solubility limit will take the longest time to crystallize since the driving force is low.

SUMMARY OF THE INVENTION

A technique has now been found which allows for the determination of concentration or solubility in a multi-component system using Raman spectroscopy. The present invention circumvents the necessity of constructing a calibration curve in order to analytically determine the concentration/solubility of a solute in a homogeneous liquid or a homogeneous solid.

In a first aspect, a procedure is utilized to determine the concentration of a solute in a multi-component mixture. Initially, a signature solute spectrum is taken in a solvent, which yields a clear Raman spectrum of the solute molecule. Then, the calibration library is constructed via the acquisition of single-component Raman spectra. Following the completion of the calibration library, a Raman spectrum of the desired unknown sample is acquired. The spectral peaks and intensities unique to the solute molecule are identified and compared with single-component Raman spectra. The ratio of components in the unknown sample is supplied to a computer, a comparison of the Raman peaks and intensities with the multi-component Raman spectrum is completed, and the concentration or solubility is calculated.

In a first embodiment, the present invention can include a known mixture in the liquid state. In another embodiment, the known mixture can exist in the solid state.

In another embodiment, the known mixture comprises a solute distributed throughout two or more excipients, solvents, or enhancers.

In another embodiment, a method of determining the saturation concentration ($C_{sat}$) of a solute in a polymer matrix or a polymer matrix film comprises:
 (a) obtaining a calibration curve;
 (b) preparing samples with high solute concentration;
 (c) allowing said samples to reach equilibrium;
 (d) finding a crystal within said polymer matrix or polymer matrix film;
 (e) scanning a laser beam off the face of the crystal; and
 (f) determining $C_{sat}$ at the crystal interface.

DETAILED DESCRIPTION OF THE INVENTION

Figure 1A:
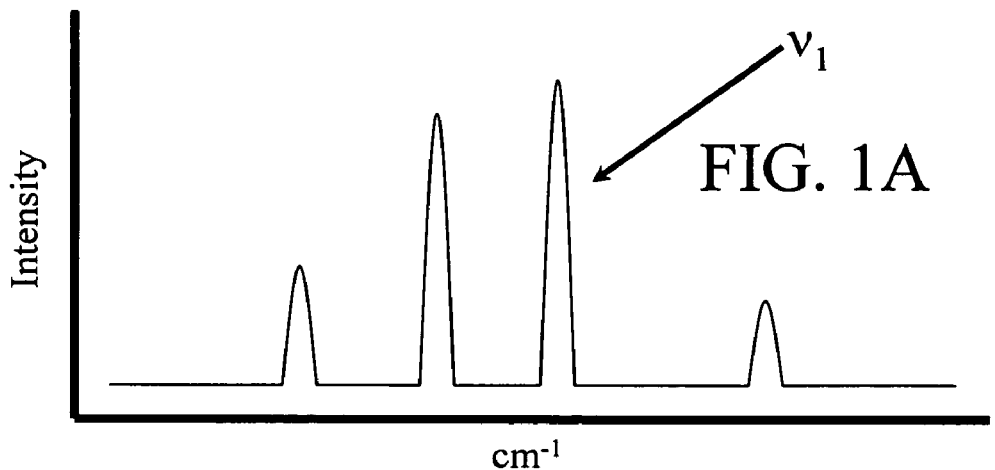
FIGS. 1A-E: Signature spectrum, single-component spectra, multi-component spectrum, and analysis of a two-component system

Traditional methods of determining the solubility or concentration of a solute in a solution or mixture have required the preparation of several standards, each of which must be identical to the solution or mixture of interest save the solute concentration, and the construction of a standard calibration curve. Generally, the standard calibration curve is generated by plotting the quantitative response of a spectroscopic technique as a function of the solute concentration of the prepared standards. Two major drawbacks of this method are its low efficiency and its high cost in materials. The preparation of standards and the construction of a standard calibration curve are required for each solution or mixture comprised of components that are not identical to those of the standards. Any change in the components themselves or their relative ratios requires the preparation of new standards and a new standard calibration curve.

The present invention allows one to measure the solubility/concentration of solutions or mixtures with multiple combinations of components or diverse relative ratios of components, or both, using calibration data consisting of only single-component samples.

High-throughput screening in the pharmaceutical, agricultural, and semiconductor industries has expanded the power and breadth of combinatorial chemistry. These vast arrays of new permutations then demand fast and accurate assessment of the key quality factors motivating the search. In particular, the pursuit for advanced formulations in drug dissolution requires a quantitative measure of the concentration of an API in solution. Parameters such as solution temperature, optical transparency, viscosity, and solvent composition can complicate matters further limiting the speed and applicability of any measurement technique.

In one aspect, this invention is a non-invasive Raman spectroscopic process that overcomes some of these obstacles incorporating a wide array of excipients, solvents, or enhancers homogeneously mixed with the solute target molecule. One of the advantages of this invention focuses on the preparative work that involves only a calibration of the solute Raman signal in single-component systems. These calibration "building blocks" of Raman signal modification variables for single-components can be gathered and then used to decipher the experimental Raman signal correlating to the solute concentration in a multi-component system.

The present invention provides for a method of measuring the concentration or solubility of a solute in a homogeneous multi-component system. The present invention enables a measurement of concentration or solubility without the consuming task of generating a standard calibration curve. The quantitative measurement can be used to determine the optimal concentration of solute (e.g., an API) to use in making formulations as well as to determine the residual concentration of solute in the presence of excipients, solvents, and enhancers.

As used herein and unless otherwise indicated, the term "multi-component" or "unknown" sample is defined to be a homogeneous liquid or a homogeneous solid composition at room temperature, in which a solute is dissolved, solvated, suspended, or dispersed in a mixture of two or more additives (e.g., excipients, solvents, or enhancers). The volumetric ratio of additives must be known in order to determine the concentration or solubility of solute. Generally, it is a multi-component system whose ultimate quantitative analysis is sought.

As used herein and unless otherwise indicated, the term "single-component" or "calibration" sample is defined to be a homogeneous liquid composition at room temperature, in which a solute is dissolved, solvated, suspended, or dispersed in a single additive (e.g., excipient, solvent, or enhancer). The concentration of solute in the additive must be known for a member of the calibration library.

As used herein and unless otherwise indicated, the term "signature" spectrum is a Raman spectrum of a sample which consists of the solute molecule of interest dissolved in a suitable solvent. Raman peaks characteristic of a given solute molecule are initially determined from such a signature spectrum.

As used herein and unless otherwise indicated, the term "solubility" is defined to be the solute concentration at the point of saturation at a given temperature. Solubility can also be described as the solute concentration of a solution under specified conditions wherein the quantity of the solute in contact with solution is not a significantly limiting factor of the solute concentration. For instance, where a solid compound is added to a solvent and solid compound remains undissolved after a specified period of time.

As used herein and unless otherwise indicated, the term "concentration" of a homogeneous liquid or solid composition is defined to be the amount (mass) of solute dissolved, solvated, suspended, or dispersed in a specified volume. Concentration can be reported in milligrams per milliliter (mg/mL), grams per liter (g/L), molarity (M), or any other units known to one of ordinary skill in the art.

As used herein and unless otherwise indicated, the term "solute" is defined to be a compound that is attempted to be dissolved, solvated, suspended, or dispersed in a liquid or a solid, either pure or in a mixture of components. For example, an API can be the solute in a pharmaceutical formulation. Generally, it is this species whose concentration and/or solubility is sought to be determined.

As used herein and unless otherwise indicated, the term "calibration curve" or "standard calibration curve" is defined to be a plot of a quantitative response (analytical measurement) of several standard samples with known concentration as a function of solute concentration. Each standard must contain both identical components and an identical ratio of components to that of the solution or mixture of interest (except for solute concentration). Every solution or mixture of interest containing a difference in either the components used or the relative ratio of components included requires an additional set of standards and corresponding calibration curve. The analytical measurements can be accomplished via UV-Visible absorption spectroscopy, fluorescence spectroscopy, or any other quantitative technique known in the art. Once this plot is constructed, the concentration of an unknown sample (identical composition to the standards, except for solute concentration) can be determined from its quantitative response. This technique is limited in that only intermediate concentrations can reliably be measured using the calibration curve, and it is both inefficient and resource intensive in cases where several unknown samples to be measured comprise distinct additive combinations.

In a first aspect, the present invention provides a method for the analytical determination of the concentration or solubility of a solute in a homogeneous multi-component system comprising the steps of:

(a) obtaining a Raman spectrum of the solute molecule in a suitable solvent;
(b) obtaining Raman spectra of appropriate single-component samples;
(c) obtaining a Raman spectrum of the multi-component sample;
(d) identifying spectral peaks and intensities unique to the solute molecule;
(e) comparing the spectral peaks and intensities unique to the solute molecule with the single-component Raman spectra;
(f) supplying a computer with a ratio of components in the multi-component system;
(g) comparing the results of step (e) with the multi-component Raman spectrum; and
(h) calculating a value for the quantitative measurement.

The measurement techniques of concentration and of solubility of the present invention include a number of steps, and incorporate a multi-component system. The multi-component system is one in which the volume ratio of the additives is known. For example, a binary system of 10 mL dimethyl sulfoxide and 30 mL methanol is a known mixture due to the established ratio (1:3) of dimethyl sulfoxide to methanol. Ternary, quarternary, and higher order known mixtures are also included in the present invention. The concentration or solubility of a solute that is homogeneously dissolved, solvated, suspended, or dispersed in a known mixture can be measured according to the present invention. The concentration or solubility of a solute that is homogeneously dissolved, solvated, suspended, or dispersed in a polymer matrix can also be determined via employment of this invention. The known mixture or polymer matrix may be a liquid or a solid at room temperature.

The typical lower limit of detection ranges from about 1 to about 20 mg/mL depending on the solute. This range is primarily due to variability in the Raman signal intensity from one solute molecule to another.

Unlike many known techniques, the present invention does not require a multitude of standard samples to be prepared where each has a similar composition to the unknown sample whose concentration or solubility is to be measured. Instead, only a calibration of the solute in each of the components (single-component systems) is required. Once a calibration library of the solute in each single-component is completed, the concentration or solubility of the solute can be determined in any multi-component system which consists of any ratio of any combination of single-components included in the calibration library. Binary systems, according to the present invention, consist of a solute dissolved, solvated, suspended, or dispersed in a mixture of two other distinct components. For instance, a binary system can consist of acetaminophen, dimethyl sulfoxide, and methanol where the concentration or solubility of acetaminophen is to be determined for a particular mixture of dimethyl sulfoxide and methanol. Upon gathering a calibration library of the single-component systems of acetaminophen in dimethyl sulfoxide and of acetaminophen in methanol, the concentration or solubility of acetaminophen in a mixture consisting of any ratio of dimethyl sulfoxide to methanol can be determined.

In the case of a ternary system, a calibration measurement of solute in each of the three components of the system is required to complete the library. Once these data are acquired, the data can be used to determine the concentration or solubility of solute in any ratio of the three components of the ternary system. Quarternary and higher order systems are likewise prepared for analysis and the same analytical measurements can be determined thereafter.

In addition to binary, ternary, and higher order systems, the removal or addition of one or more components in a multi-component sample is also tolerated by employment of the present invention. For example, upon completion of a calibration library for a given ternary sample (i.e., a solute dissolved in a known ratio of three components), the concentration of solute in any binary system comprised from members of the library or any single excipient, solvent, or enhancer can also be determined. Furthermore, the calibration library can be supplemented with additional single-component samples to include quarternary and higher order samples as viable samples for the determination of concentration using methods of the present invention.

Compatibility issues can arise for some solute/single-component combinations. For example, a given solute (e.g., API) may not be soluble in every single-component of a multi-component system. Another example comes about when the concentration of a single-component sample is not accurately known due to its low solubility in a given additive. Also, a solute (e.g., API) with low solubility in a single-component may yield a Raman signal that is too weak to be detected. In such instances, a mixture of the problematic additive and another, more effectual, additive may be employed to take the place of the corresponding single-component system in the calibration library.

The calibration library is a collection of the single-component system Raman spectra that correspond to a particular solute molecule in a multi-component system or a set of multi-component systems. Each single-component system consists of a solute and a single additive (e.g., excipient, solvent, or enhancer) with a known concentration of solute. This single-component system is analyzed via Raman spectroscopy and the Raman spectrum (calibration spectrum) is saved as one member of the calibration library for a particular solute molecule.

This invention enables high-throughput concentration and solubility measurements performed non-invasively within a large library of excipients, solvents, and enhancers for a specific solute (e.g., an API). The construction of such a calibration library allows one to maximize quantitative concentration/solubility measurements in highly diverse formulations and also permits fast throughput of sample analysis. The number of components, the identity of components, and the ratio of components can all be varied while allowing the concentration or solubility of a solute to be measured consistently, accurately, and rapidly.

Once a calibration library has been completed for a solute molecule, the concentration or solubility of a corresponding multi-component system can be determined. The calibration spectra are convoluted to form a model for the Raman signal in an assortment of additive mixtures. The concentration or solubility of the multi-component system is determined by comparison of common Raman scattering peaks known to be characteristic of the solute in both the single-component system calibration spectra and in the multi-component system spectrum.

The characteristic (signature) solute peaks in both single-component and multi-component system Raman spectra are determined from a signature spectrum. A signature spectrum is a Raman spectrum of a sample which consists of the solute molecule of interest dissolved in a suitable solvent, and is appreciated by those skilled in the art. FIG. 1A depicts a signature Raman spectrum of a particular solute molecule. Four Raman scattering peaks are present in FIG. 1A, and it is these characteristic peaks which are used to find all common solute peaks. Common solute peaks are those which can be found in each of the signature spectrum, the calibration spectra, and the unknown sample spectrum. A spectral peak is considered to be a common peak if it does not shift (from signature spectrum to single-component or multi-component spectrum) its position from the signature spectrum by more than about 2.5 cm$^{-1}$ (blueshifted or redshifted) and it does not overlap with an existing peak from the solvent system.

The hardware for the Raman system can follow general practice in laser microscopy. A monochromatic or nearly monochromatic light source in the visible or IR electromagnetic spectrum is guided and focused into the sample container. This light beam can be guided by metallic or dielectric mirrors or by fiber optic waveguides. Moreover, this container can be a vial, a plate, a reaction chamber, a flask, a cuvette etc. The scattered light is then collected into a spectrometer to spectrally resolve the scattered light and to remove the excitation light. A photodetector is employed to collect the scattered light and measure its intensity at the desired wavelengths. These include but are not limited to Si/Ge photodiodes, charge-coupled device (CCD) cameras, and photomultiplier tubes (PMT). The light source can be from a Ti:Sapphire laser, an ionized gas laser, a solid state semiconductor laser, a lamp source filtered to produce monochromatic or nearly monochromatic light, or any other light source known to those skilled in the art.

The samples are not limited to a set composition since the search for new formulations requires expanding to new additive space for enhanced dissolution performance. Miscibility of additives in a given formulation can be verified before, during, or after, the Raman spectrum is acquired. The solutions are homogeneously mixed in the container by the time the measurement is conducted. The inelastically scattered light from the laser is then collected and coupled to a monochromator, which spectrally resolves the light. Other spectrally resolving instruments include holographic dispersing prisms, gratings, etc. This spectrum is projected onto a photodetector and the data are transferred to a computer.

The raw spectra are collected with typical acquisition times of about 10, about 15, about 20, about 25, about 30, about 35, about 40, about 45, about 50, about 55, or about 60 seconds. The acquisition times can however be greater or less than that above due to laser intensity at the sample, strength of Raman signal from the solute molecules or other controlled or inherent factors. Although the raw spectra can include background fluorescence, broad peaks due to the curvature of the sample, or other undesirable spectral artifacts, these features can be filtered out through a band pass filtration algorithm. For example, filtering techniques as described in US Publication No. 2003/0138940 can be used to reject noise. A spectrum filter removes slowly changing features such as background fluorescence and fits the sharp features to a peak fitting routine. Filtering of raw Raman spectra can be completed using any one or more of many techniques known to those of ordinary skill in the art.

Figure 1B:
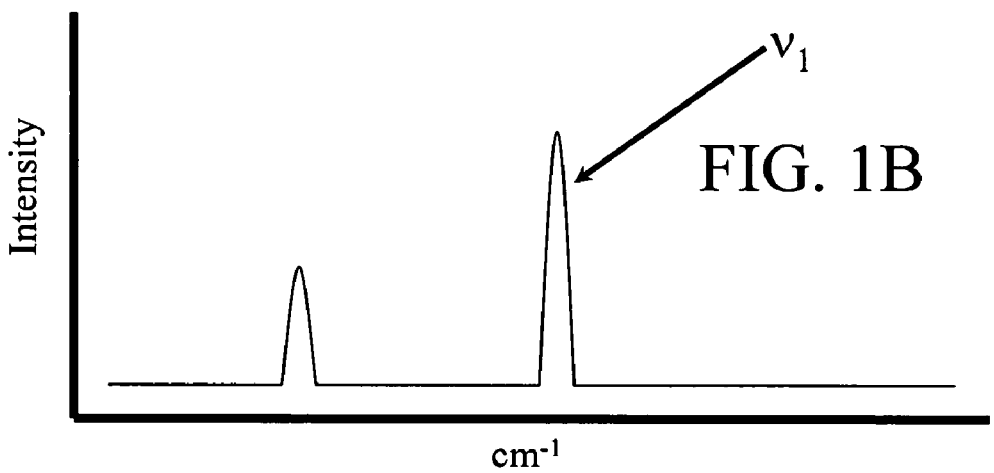
Figure 1C:
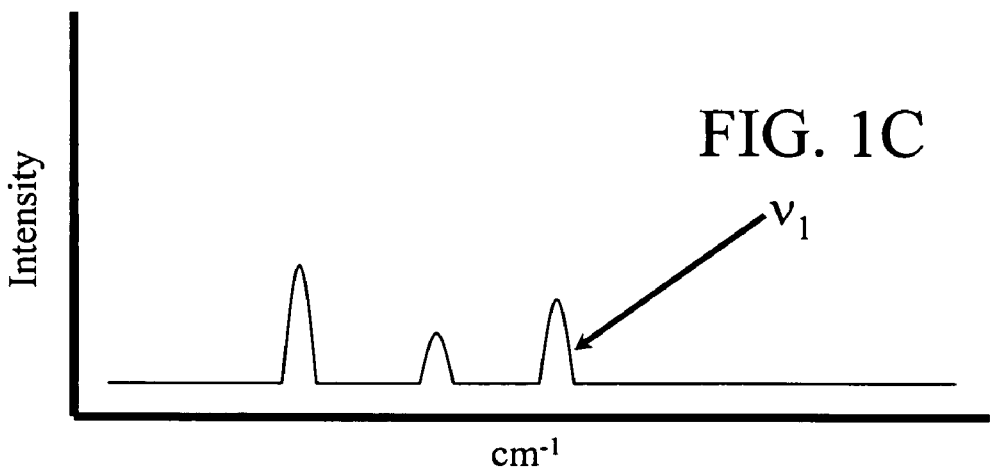
Figure 1D:
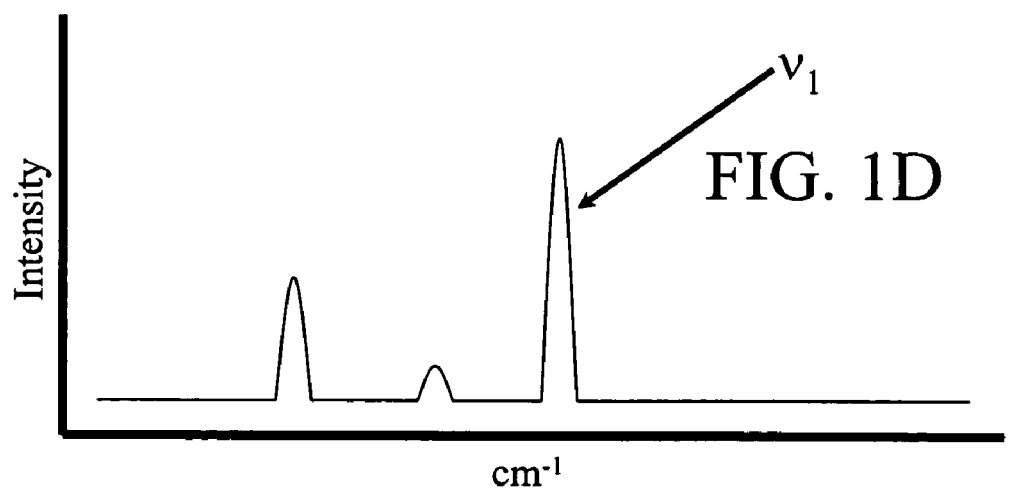
Figure 1E:
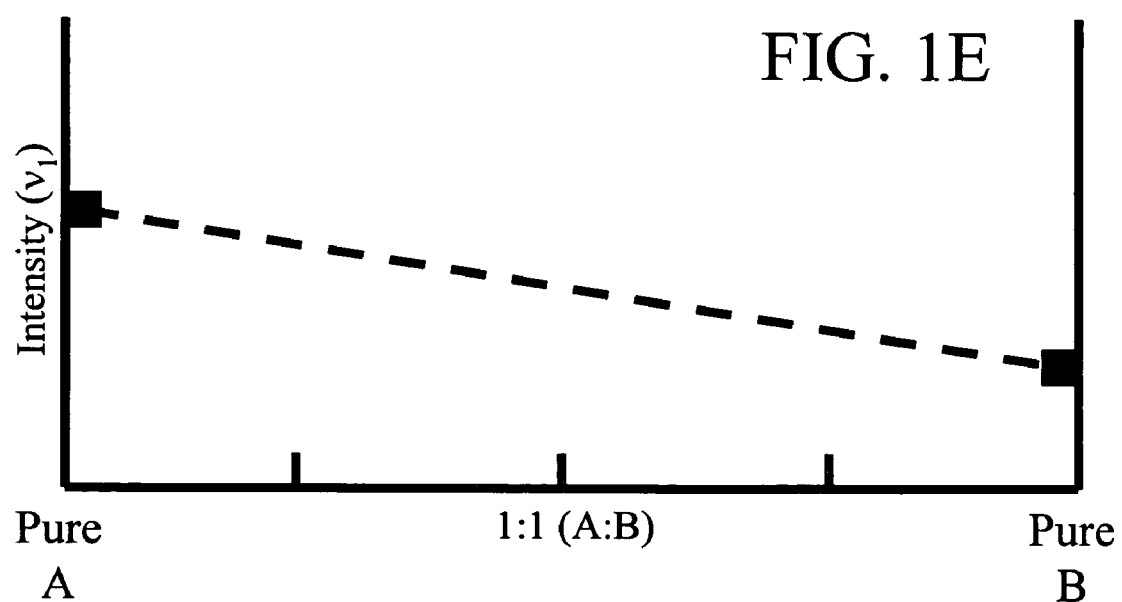

FIGS. 1B and 1C depict calibration spectra for a two-component system (component A and component B) in which the solute from FIG. 1A is homogeneously distributed. FIG. 1B represents a calibration spectrum for single-component A while FIG. 1C represents a calibration spectrum for single-component B. The concentration of both single-component systems is 15 mg/mL. FIG. 1D depicts a Raman spectrum of the two-component system (A and B) with an unknown solute concentration. The ratio of A:B is 1:1 in the unknown sample. FIG. 1E is a representation of the Raman intensities at a particular frequency ($v_1$) in both calibration spectra. A dotted line has been drawn between the calibration intensities and illustrates the expected Raman intensities at frequency $v_1$ due to the solute molecule in mixtures of both components. This line displays the expected Raman intensities for solute molecules in mixtures of components A and B at a concentration of 15 mg/mL. In view of FIG. 1E, the ratio of components in the unknown sample can be used to determine the concentration of solute. In the present example, an A:B component ratio of 1:1 will result in a Raman signal intensity (at frequency $v_1$) of $(I_A+I_B)/2$ where the concentration of solute is 15 mg/mL. A solute concentration above 15 mg/mL results in a Raman intensity greater than $(I_A+I_B)/2$ while a solute concentration below 15 mg/mL results in a Raman intensity less than $(I_A+I_B)/2$. Due to a directly proportional and linear relationship between Raman scattering intensity and concentration, values both above and below 15 mg/mL are easily calculated based on the measured Raman intensity of the unknown (multi-component) sample.

In another embodiment, automated software can be programmed to analyze the data. First, the software identifies the spectral peaks and intensities that are unique to the solute molecule by direct comparison with a solvent only (signature) spectrum. The various single-component (calibration) Raman spectra are then accessed and a calibration matrix is configured and saved from these single-component data. The calibration matrix consists of the calibration spectra required to analyze a particular unknown sample or set of unknown samples. The computer then derives the relative ratio of the various components in the unknown sample and calculates a concentration of the solute in the unknown sample. The spectral comparison uses all the common solute peaks available in any additive combination, normalized by weight to their relative peak intensities. The concentration of solute in the multi-component system is calculated using a weighted average determination. For instance, the concentration (C) of a solute in a multi-component system can be calculated by using equation (1), $$C = a_1 c_1 + a_2 c_2 + a_3 c_3 + \ldots \quad (1)$$

where $a_1$ is the normalized intensity of a common spectral peak ($v_1$) from the unknown sample Raman spectrum, $c_1$ is the predicted concentration of the unknown sample based solely upon the common spectral peak $v_1$, $a_2$ is the normalized intensity of a common spectral peak ($v_2$) from the unknown sample Raman spectrum, $c_2$ is the predicted concentration of the unknown sample based solely upon the common spectral peak $v_2$, $a_3$ is the normalized intensity of a common spectral peak ($v_3$) from the unknown sample Raman spectrum, and $c_3$ is the predicted concentration of the unknown sample based solely upon the common spectral peak $v_3$. The sum of the normalized intensities (e.g., $a_1+a_2+a_3$) is equal to 1. Many chemometric methods are described in the prior art and can be applied to improve the robustness and accuracy of the measurements described herein.

This invention can also incorporate physical parameters unique to the chemical additives such as hydrogen bonding, dipole polarity, steric hindrance, solubility limits in liquids or solids, or other physical properties that bias their impact on the target Raman signal.

In the pharmaceutical and medical device industry, for example, APIs are often present and co-dissolved with polymers in drug delivery devices. Polymeric matrices that contain one or more APIs often serve multiple functions such as, but not limited to: 1) acting to control the release of drug temporally; 2) controlling the delivery of drug in the appropriate pH or environment; 3) increasing the chemical potential of the compound by holding it in solution as an amorphous form; or 4) acting as a mechanical scaffold or a bonding medium. In each of these uses, the saturation API concentration in the polymer system is important in dictating the overall drug delivery properties.

In another embodiment of the present invention, the solubility of a solute (e.g., an API) in a polymer matrix or in a polymer matrix film can be determined. The technique is quantitative, non-destructive, and suitable for high-throughput characterization of drug delivery formulations such as, but not limited to, transdermal matrices, drug-eluting coatings, and controlled release reservoirs. The solute solubility is important to determine in HT formulation screening and development because it can dictate release kinetics, mechanical properties, and biocompatibility of the system as a whole.

In another embodiment, a method of determining the saturation concentration ($C_{sat}$) of a solute in a polymer matrix or a polymer matrix film comprises:

(a) obtaining a calibration curve;
(b) preparing samples with high solute concentration;
(c) allowing said samples to reach equilibrium;
(d) finding a crystal within said polymer matrix or polymer matrix film;
(e) scanning a laser beam off the face of the crystal; and
(f) determining $C_{sat}$ at the crystal interface.

In another embodiment, the calibration curve in step (a) comprises the intensity between the solute signal and the polymer matrix or polymer matrix film for each formulation. In another embodiment, the calibration curve in step (a) comprises the normalized intensity between the solute signal and the polymer matrix or polymer matrix film for each formulation. In another embodiment, the calibration curve in step (a) is constructed using several low solute level samples, for example, 3, 4, 5, 6, 7, 8, 9, or 10 or more samples. See, e.g., FIG. 10.

In another embodiment, the samples in step (b) are prepared with high solute concentration and a high driving force to nucleate. In another embodiment, the samples in step (b) are prepared with seed crystals.

In another embodiment, the crystal in step (d) is found using an in-line vision station. In another embodiment, the crystal in step (d) is found using, for example, but not limited to, a camera, a CCD camera, or a microscope.

In another embodiment, the laser beam in step (e) is scanned in increments. In another embodiment, the laser beam in step (e) is scanned in increments of at least about 1.0 micrometer. For example, the laser beam can be scanned in increments of about 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 25.0, 30.0, 35.0, 40.0, 45.0, or 50.0 micrometers.

In another embodiment, $C_{sat}$ is determined by analyzing a Raman signal at the interface. In another embodiment, $C_{sat}$ is determined by analyzing a normalized Raman signal at the interface.

As defined herein, the "minimum boundary concentration" is the concentration of solute dissolved in a polymer matrix or a polymer matrix film in a sample, prepared at a supersaturated concentration, prior to or at equilibrium. The minimum boundary concentration of a supersaturated sample approaches $C_{sat}$ over time.

As defined herein, the term "high solute concentration" is defined as a concentration at least about 1.5 times the saturation concentration ($C_{sat}$). For example, about 1.5, 2.0, 2.5, 3.0, 3.5, 4.0, 4.5, or 5.0 times $C_{sat}$ or more or any intermediate value is defined as a high solute concentration. In certain embodiments, the high solute concentration can be limited to less than about 20, 25, 30, 35, 40, 45, or about 50 percent by weight of the total formulation. In another embodiment, the high solute concentration does not exceed about 50 percent by weight of the total formulation.

APIs, acrylic polymer, and other additives can be processed into arrays of planar transdermal delivery films and the solubility of the API in each unique formulation can be determined. The present invention comprises a laser Raman spectroscopy and imaging system which is developed to achieve high sensitivity and to map API concentration in polymer films and matrices. Sample formulations can be fabricated with high API content in order to induce crystal formation. A focused laser beam can then be used to scan across the crystal-bulk boundary to obtain a concentration profile. This profile can then be used together with one or more calibration curves to calculate the API saturation concentration ($C_{sat}$) in the bulk polymer phase.

Figure 7:
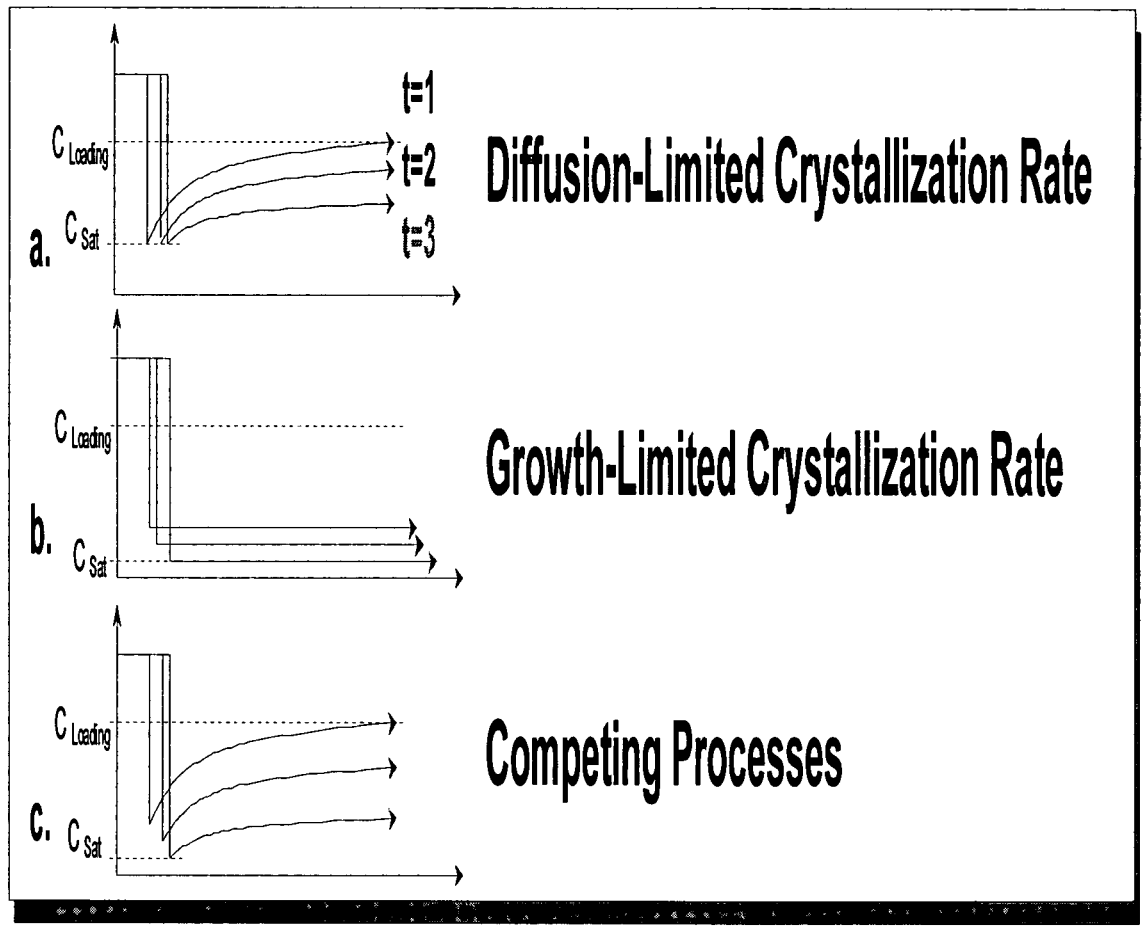
FIG. 7: Solute concentration profiles of three classifications of formulations

Once nucleation has occurred, the solute can continue to diffuse to the crystal surface until the concentration in the bulk comes to equilibrium. If the crystal grows readily and the diffusion to the crystallization site is rate-limiting, then the saturation concentration is maintained at the crystal interface during growth. This solute concentration profile is shown in the top scheme of FIG. 7 (section a.). If the diffusion occurs readily, but the crystal growth rate is rate-limiting, the solute concentration profile resembles that shown in the middle scheme of FIG. 7 (section b.). Finally, the bottom scheme of FIG. 7 (section c.) shows the profile for an intermediate regime. In diffusion-limited crystal growth, the minimum concentration at the boundary of the crystal face and the bulk formulation is expected to remain constant and equal to $C_{sat}$. In mixed mode or growth-limited crystallization, this value could decrease over time until equilibrium is reached throughout the film. In addition, the samples can be monitored for crystallization by visual observation under cross-polarized lighting.

In another embodiment, the apparatus used in determining the saturation concentration of a solute in a polymer matrix or a polymer matrix film, optionally comprises one or more of the following: a pump laser, a Ti:sapphire laser, a beam splitter, an auto-focusing objective lens, an automated positioning stage, an array of polymer samples, a notch filter, or a CCD camera.

Any of the above methods can be employed to study one or more samples. For example, a plurality of samples (2, 3, 4, 8, 16, 32, 64, 96, 128, 256, 512, 1024 samples or more) or an array of samples can be analyzed using any of the above methods. Such methods can be used for the high-throughput analysis of many liquid, solid, and/or polymeric samples.

EXEMPLIFICATION

Example 1

Acetaminophen in 1:3 Binary Mixtures

Acetaminophen was dissolved in various single component excipients listed below at a concentration of 10 mg/mL. The single component excipients included: dimethyl sulfoxide (DMSO), acetone, isopropanol (IPA), methanol, acetonitrile (AcN), tetrahydrofuran (THF), water, and 1,2-dioxane. Following the preparation of the single component solutions, the solutions were mixed at 1:3 ratios by volume. A list of the binary mixtures in 1:3 ratios of excipients is found in Table I.

TABLE I

Acetaminophen in 1:3 Binary Mixtures

| 1:3 Ratio | DMSO | Acetone | IPA | Methanol | Acetonitrile | THF | Water | 1,2-Dioxane |
|---|---|---|---|---|---|---|---|---|
| DMSO | 1 | 2 | 3 | 4 | 5 | 6 | 7 | 8 |
| Acetone | 9 | 10 | 11 | 12 | 13 | 14 | 15 | 16 |
| IPA | 17 | 18 | 19 | 20 | 21 | 22 | 23 | 24 |

TABLE I-continued

Acetaminophen in 1:3 Binary Mixtures

| 1:3 Ratio | DMSO | Acetone | IPA | Methanol | Acetonitrile | THF | Water | 1,2-Dioxane |
|---|---|---|---|---|---|---|---|---|
| Methanol | 25 | 26 | 27 | 28 | 29 | 30 | 31 | 32 |
| Acetonitrile | 33 | 34 | 35 | 36 | 37 | 38 | 39 | 40 |
| THF | 41 | 42 | 43 | 44 | 45 | 46 | 47 | 48 |
| Water | 49 | 50 | 51 | 52 | 53 | 54 | 55 | 56 |
| 1,2-Dioxane | 57 | 58 | 59 | 60 | 61 | 62 | 63 | 64 |

As indicated in Table I, sample 1 is a 1:3 mixture of DMSO:DMSO, sample 2 is a 1:3 mixture of DMSO:acetone, sample 3 is a 1:3 mixture of DMSO:IPA, and so on.

Figure 2A:
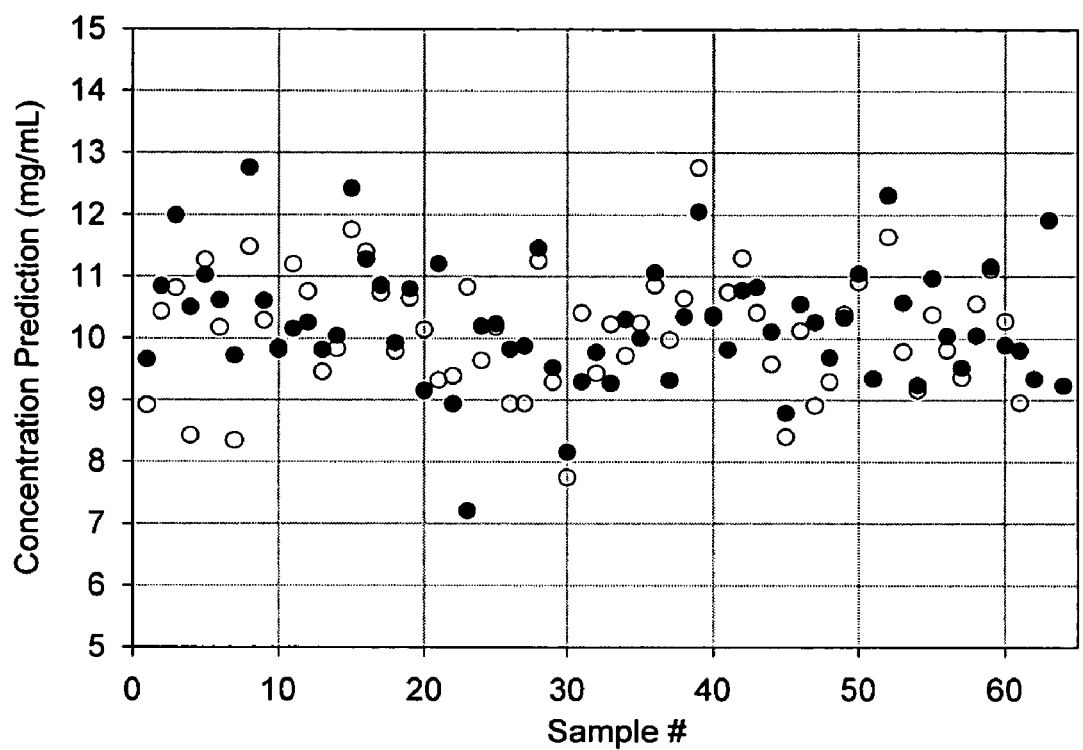
FIGS. 2A-B: Acetaminophen in 1:3 binary mixtures
Figure 2B:
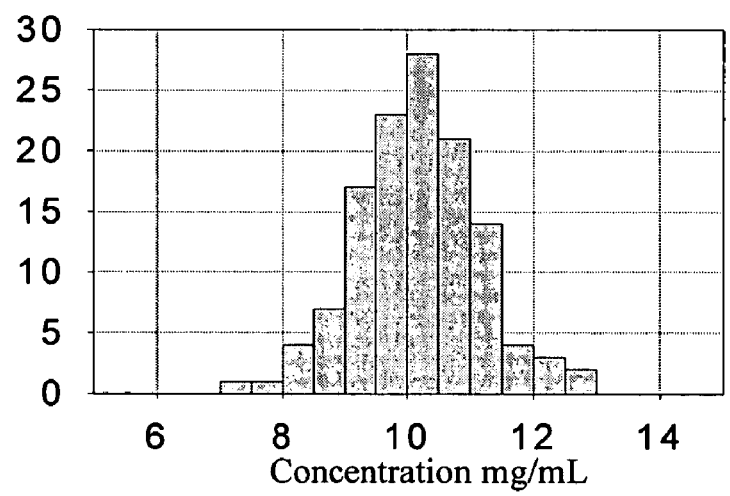

Sample vials were loaded into a vial holder and the laser was focused into the liquid portion. In cases where solid particles may be present, the laser would be directed to a clear liquid area. The Raman spectrum was collected for 30 seconds exposure (3×10 seconds integration time) and the software filtration and calibration performed. FIG. 2A shows the relative accuracy in the measurement for two trials of various binary mixtures. The mean value for the concentration is 10.18 mg/mL and the relative standard deviation (RSD) is 9.6 percent. FIG. 2B shows the distribution of measured concentrations of acetaminophen in various 1:3 binary mixtures.

Example 2

Acetaminophen in 1:1:1 Ternary Mixtures

Acetaminophen was dissolved in various single component excipients listed below at a concentration of 10 mg/mL. The single component excipients included: isopropanol (IPA), acetone, methanol (MeOH), acetonitrile (AcN), and water. Following the preparation of the single component solutions, the solutions were mixed at 1:1:1 ratios by volume. A list of the binary mixtures in 1:1:1 ratios of excipients is found in Table II.

As indicated in Table II, sample 1 is a 1:1:1 mixture of IPA:acetone:acetone, sample 5 is a 1:1:1 mixture of MeOH:acetone:acetone, sample 34 is a 1:1:1 mixture of AcN:acetone:IPA, and so on.

Figure 3A:
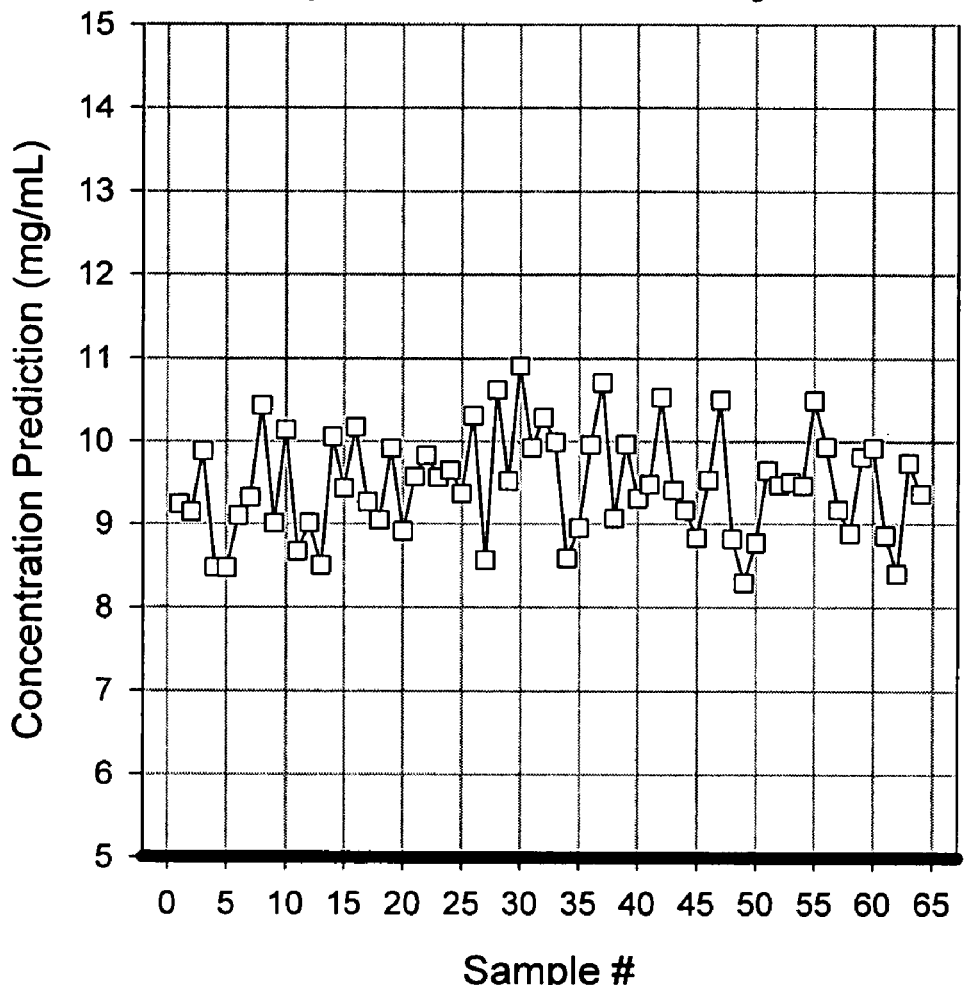
FIGS. 3A-B: Acetaminophen in 1:1:1 ternary mixtures
Figure 3B:
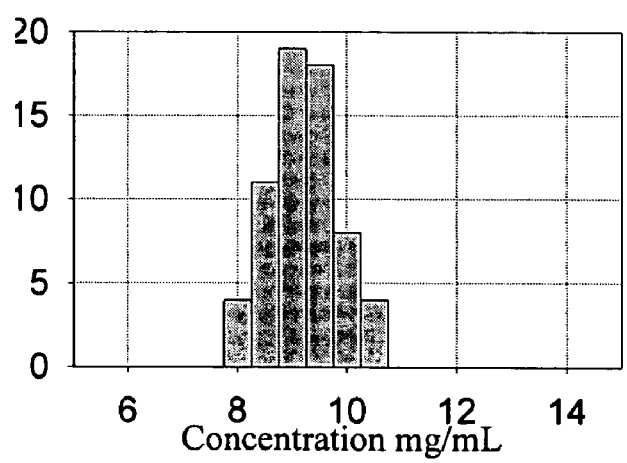

Sample vials were loaded into a vial holder and the laser was focused into the liquid portion. In cases where solid particles may be present, the laser would be directed to a clear liquid area. The Raman spectrum was collected for 30 seconds exposure (3×10 seconds integration time) and the software filtration and calibration performed. FIG. 3A shows the relative accuracy in the measurement for various binary mixtures. The mean value for the concentration is 9.48 mg/mL and the relative standard deviation (RSD) is 6.7 percent. FIG. 3B shows the distribution of measured concentrations of acetaminophen in various 1:1:1 ternary mixtures.

Example 3

Ibuprofen in 1:1 Mixtures

Ibuprofen was dissolved in various single component excipients listed below at a concentration of 10 mg/mL. The single component excipients included: tetrahydrofuran (THF), isopropanol (IPA), acetonitrile, acetone, and ethanol. Three mixtures were also prepared, including: ethanol/poloxamer, water/ethanol/PEG 400, and water/ethanol, each at 10 mg/mL ibuprofen. Following the preparation of the above

TABLE II

Acetaminophen in 1:1:1 Ternary Mixtures

| IPA | Acetone | MeOH | AcN | Water | MeOH | Acetone | IPA | AcN | Water |
|---|---|---|---|---|---|---|---|---|---|
| Acetone | 1 | 2 | 3 | 4 | Acetone | 5 | 6 | 7 | 8 |
| MeOH | 9 | 10 | 11 | 12 | IPA | 13 | 14 | 15 | 16 |
| AcN | 17 | 18 | 19 | 20 | AcN | 21 | 22 | 23 | 24 |
| Water | 25 | 26 | 27 | 28 | Water | 29 | 30 | 31 | 32 |
| AcN | Acetone | IPA | MeOH | Water | Water | Acetone | IPA | MeOH | AcN |
| Acetone | 33 | 34 | 35 | 36 | Acetone | 37 | 38 | 39 | 40 |
| IPA | 41 | 42 | 43 | 44 | IPA | 45 | 46 | 47 | 48 |
| MeOH | 49 | 50 | 51 | 52 | MeOH | 53 | 54 | 55 | 56 |
| Water | 57 | 58 | 59 | 60 | AcN | 61 | 62 | 63 | 64 | component solutions, the solutions were mixed at 1:1 ratios by volume. A list of the mixtures in 1:1 ratios of excipients is found in Table III.

TABLE III

Ibuprofen in 1:1 Mixtures

|  | THF | IPA | Acetonitrile | Ethanol/ Poloxamer | Ethanol | Acetone | Water/Ethanol/ PEG 400 | Water/Ethanol |
|---|---|---|---|---|---|---|---|---|
| THF | 1 | 2 | 3 | 4 | 5 | 6 | 7 | 8 |
| IPA | 9 | 10 | 11 | 12 | 13 | 14 | 15 | 16 |
| Acetonitrile | 17 | 18 | 19 | 20 | 21 | 22 | 23 | 24 |
| Acetone | 25 | 26 | 27 | 28 | 29 | 30 | 31 | 32 |
| Ethanol | 33 | 34 | 35 | 36 | 37 | 38 | 39 | 40 |

As indicated in Table III, sample 1 is a 1:1 mixture of THF:THF, sample 2 is a 1:1 mixture of THF:IPA, sample 3 is a 1:1 mixture of THF:acetonitrile, and so on.

Figure 4A:
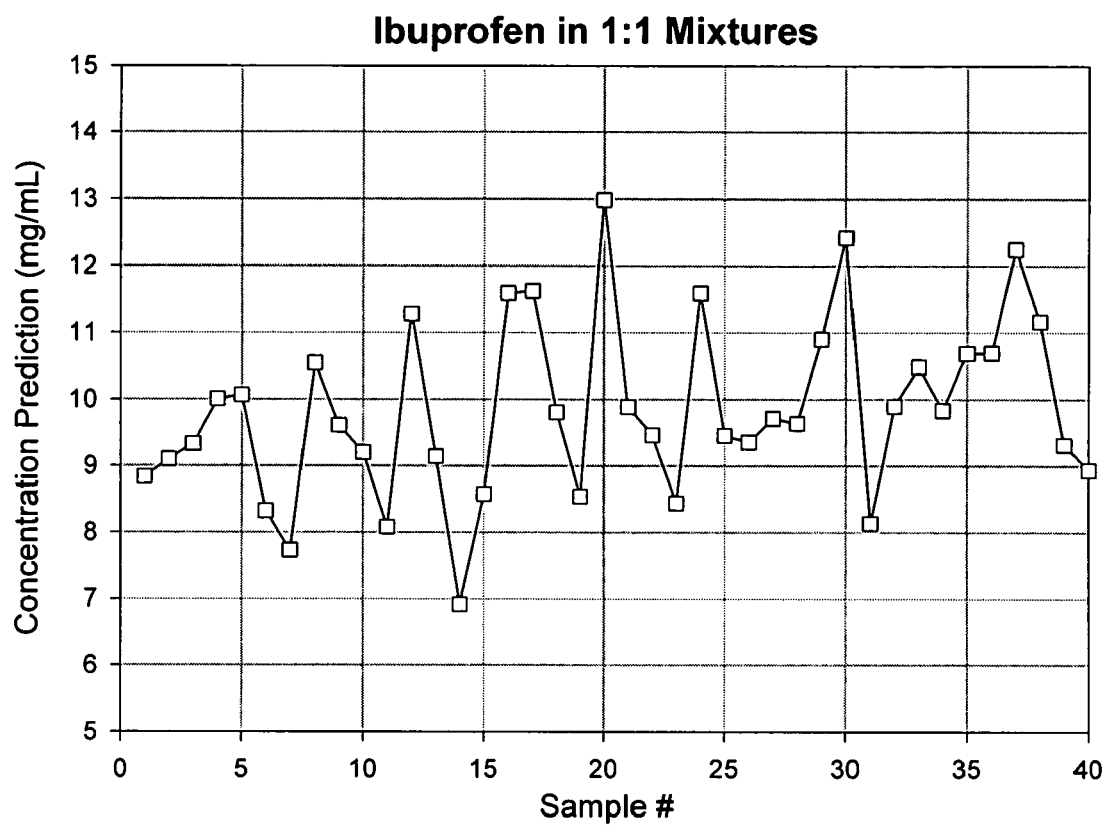
FIGS. 4A-B: Ibuprofen in 1:1 mixtures
Figure 4B:
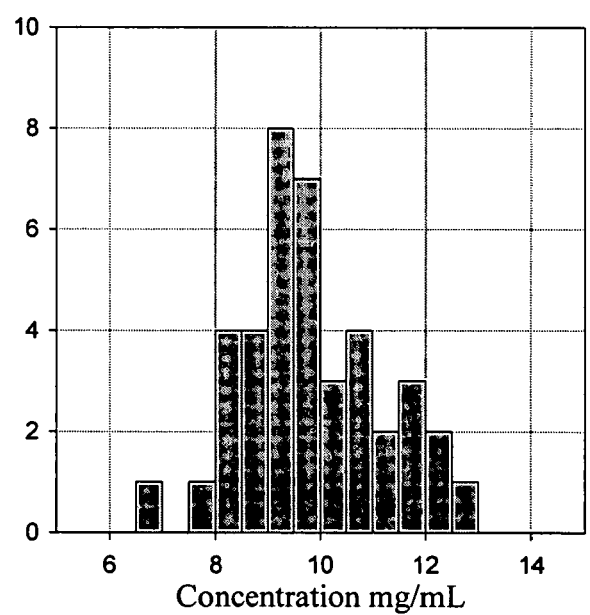

Sample vials were loaded into a vial holder and the laser was focused into the liquid portion. In cases where solid particles may be present, the laser would be directed to a clear liquid area. The Raman spectrum was collected for 30 seconds exposure (3×10 seconds integration time) and the software filtration and calibration performed. FIG. 4A shows the relative accuracy in the measurement for various binary mixtures. The mean value for the concentration is 9.84 mg/mL and the relative standard deviation (RSD) is 13.6 percent. FIG. 4B shows the distribution of measured concentrations of ibuprofen in various 1:1 mixtures.

Example 4

Acetylsalicylic Acid in 1:1 Binary Mixtures

Acetylsalicylic acid was dissolved in various single component excipients listed below at a concentration of 10 mg/mL. The single component excipients included: dimethyl sulfoxide (DMSO), acetone, isopropanol (IPA), acetonitrile, tetrahydrofuran (THF), water, and 1,2-dioxane. Following the preparation of the single component solutions, the solutions were mixed at 1:1 ratios by volume. A list of the binary mixtures in 1:1 ratios of excipients is found in Table IV.

TABLE IV

Acetylsalicylic acid in 1:1 Binary Mixtures

|  | DMSO | Acetone | IPA | Aceto- nitrile | THF | 1,2- Dioxane |
|---|---|---|---|---|---|---|
| DMSO |  | 1, 2 | 3, 4 | 5 | 6, 7 | 8, 9 |
| Acetone | 10, 11 |  | 12, 13 | 14, 15 | 16, 17 | 18, 19 |
| IPA | 20, 21 | 22, 23 |  | 24, 25 | 26 | 27, 28 |
| Acetonitrile | 29, 30 | 31, 32 | 33, 34 |  | 35, 36 | 37, 38 |
| THF | 39, 40 | 41, 42 | 43, 44 | 45, 46 |  | 47, 48 |
| 1,2-Dioxane | 49, 50 | 51, 52 | 53, 54 | 55, 56 | 57, 58 |  |

As indicated in Table IV, sample 1 is a 1:1 mixture of DMSO:acetone, sample 3 is a 1:1 mixture of DMSO:IPA, sample 5 is a 1:1 mixture of DMSO:acetonitrile, and so on.

Figure 5A:
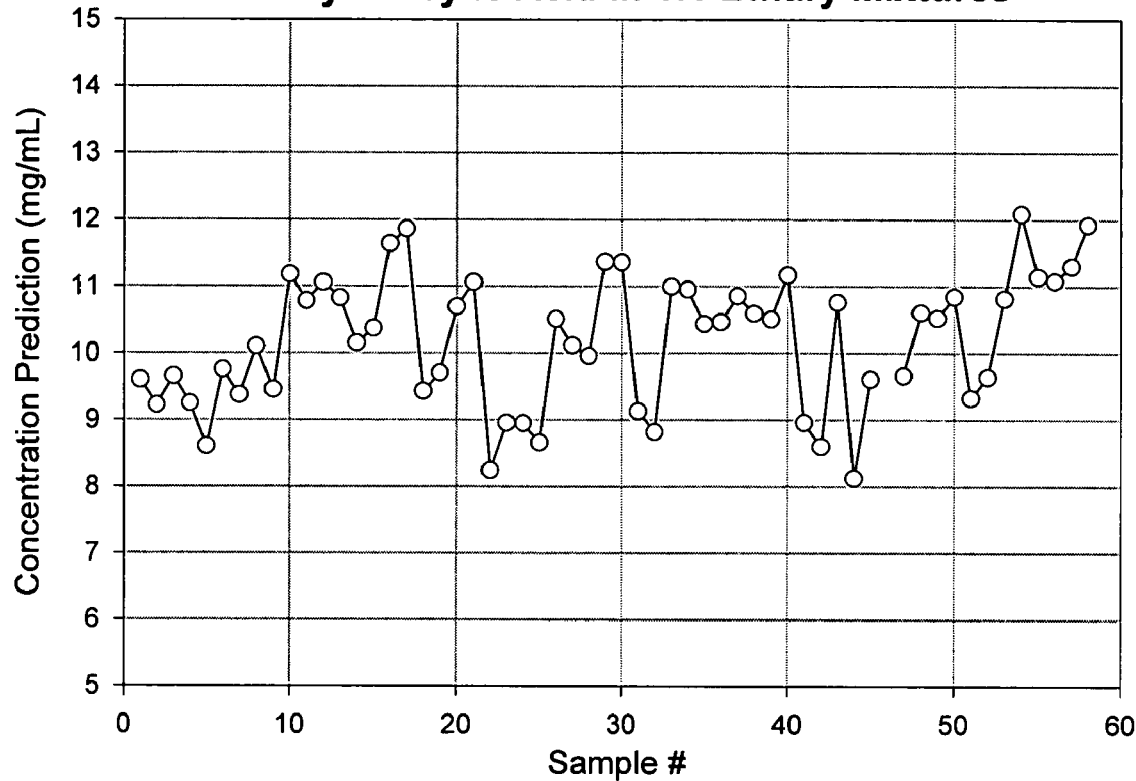
FIGS. 5A-B: Acetylsalicylic acid in 1:1 binary mixtures
Figure 5B:
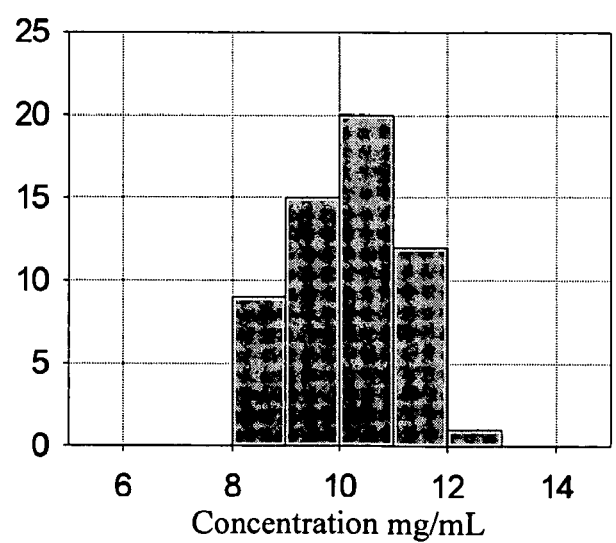

Sample vials were loaded into a vial holder and the laser was focused into the liquid portion. In cases where solid particles may be present, the laser would be directed to a clear liquid area. The Raman spectrum was collected for 30 seconds exposure (3×10 seconds integration time) and the software filtration and calibration performed. FIG. 5A shows the relative accuracy in the measurement for various binary mixtures. The mean value for the concentration is 10.19 mg/mL and the relative standard deviation (RSD) is 9.7 percent. FIG. 5B shows the distribution of measured concentrations of acetylsalicylic acid in various 1:1 binary mixtures.

Example 5

Celecoxib in 1:1 Binary Mixtures

Acetylsalicylic acid was dissolved in various single component excipients listed below at a concentration of 10 mg/mL. The single component excipients included: dimethyl sulfoxide (DMSO), acetone, isopropanol (IPA), methanol, acetonitrile, tetrahydrofuran (THF), and 1,2-dioxane. Following the preparation of the single component solutions, the solutions were mixed at 1:1 ratios by volume. A list of the binary mixtures in 1:1 ratios of excipients is found in Table V.

TABLE V

Celecoxib in 1:1 Binary Mixtures

|  | DMSO | Acetone | IPA | Methanol | Acetonitrile | THF | 1,2-Dioxane |
|---|---|---|---|---|---|---|---|
| DMSO | 1 | 2 | 3 | 4 | 5 | 6 | 7 |
| Acetone | 8 | 9 | 10 | 11 | 12 | 13 | 14 |
| IPA | 15 | 16 | 17 | 18 | 19 | 20 | 21 |
| Methanol | 22 | 23 | 24 | 25 | 26 | 27 | 28 |
| Acetonitrile | 29 | 30 | 31 | 32 | 33 | 34 | 35 |
| THF | 36 | 37 | 38 | 39 | 40 | 41 | 42 |
| 1,2-Dioxane | 43 | 44 | 45 | 46 | 47 | 48 |  |

As indicated in Table V, sample 1 is a 1:1 mixture of DMSO:DMSO, sample 2 is a 1:1 mixture of DMSO:acetone, sample 3 is a 1:1 mixture of DMSO:IPA, and so on.

Figure 6A:
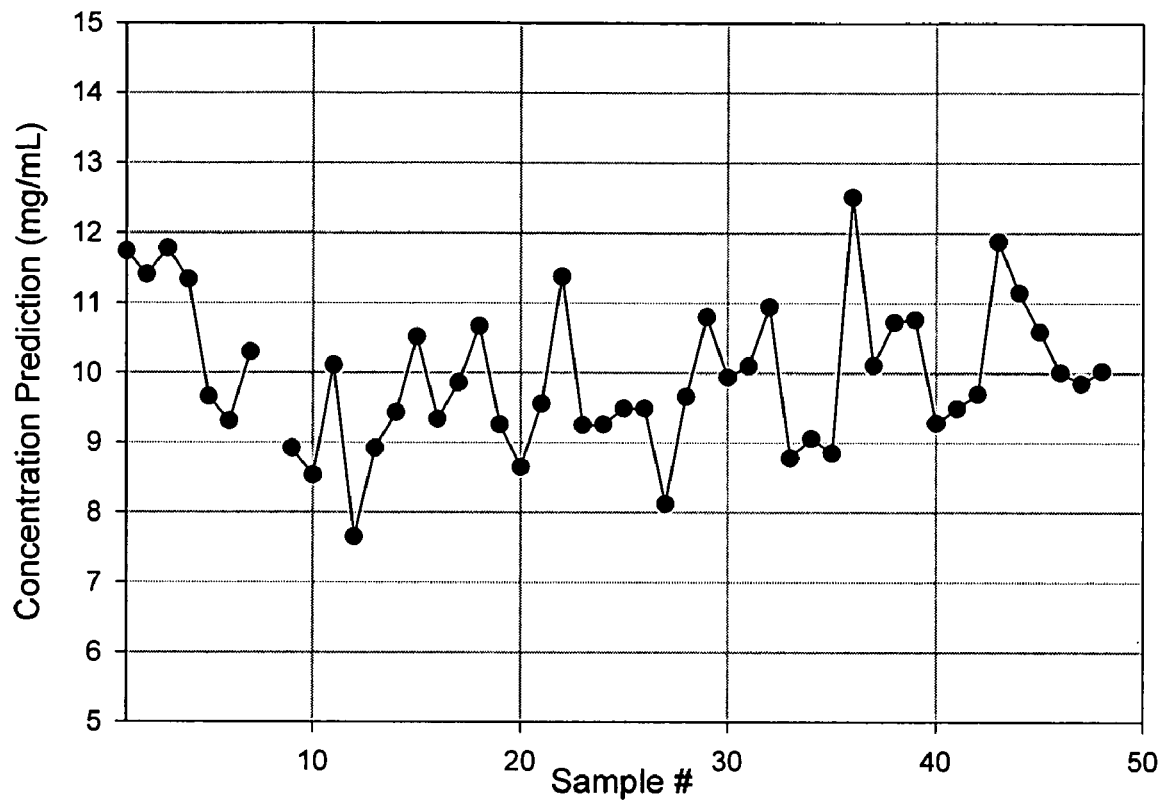
FIGS. 6A-B: Celecoxib in 1:1 binary mixtures
Figure 6B:
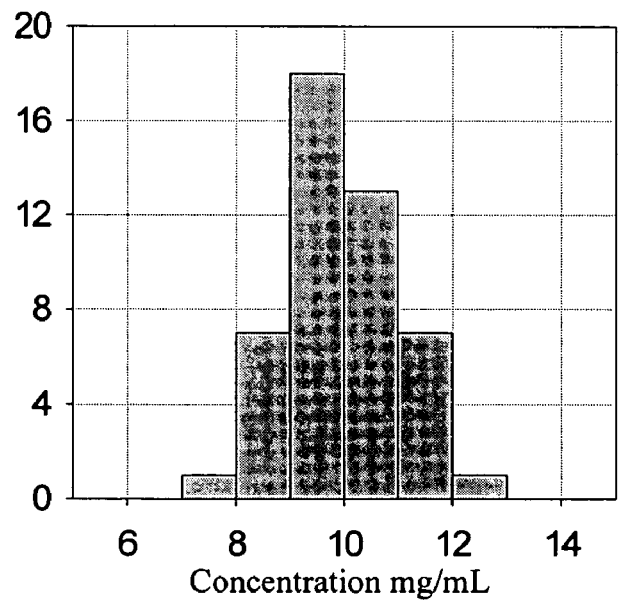

Sample vials were loaded into a vial holder and the laser was focused into the liquid portion. In cases where solid particles may be present, the laser would be directed to a clear liquid area. The Raman spectrum was collected for 30 seconds exposure (3×10 seconds integration time) and the software filtration and calibration performed. FIG. 6A shows the relative accuracy in the measurement for various binary mixtures. The mean value for the concentration is 9.96 mg/mL and the relative standard deviation (RSD) is 10.5 percent. FIG. 6B shows the distribution of measured concentrations of celecoxib in various 1:1 binary mixtures.

Example 6

Solubility of Solutes in a Polymer Film

The determination of the saturation concentration ($C_{sat}$) of a solute in a polymer matrix or a polymer matrix film was completed by: 1) obtaining a calibration curve for normalized intensity between the solute signal and the polymer matrix for each formulation by fabricating several low solute level samples; 2) preparing samples with high solute concentration and high driving force to nucleate or seed samples to force crystallization; 3) allowing three days to reach equilibrium; 4) finding a crystal within the polymer matrix with in-line vision station; 5) scanning laser beam off the face of the crystal in 10 micrometer increments; and 6) determining $C_{sat}$ with the normalized signal at the interface. The normalized intensity can be calculated using the following formula:

$$\text{Normalized Intensity} = (I_{solute}/I_{polymer}) \times C_{polymer} \quad (2)$$

where $I_{solute}$ is the Raman intensity due to the solute, $I_{polymer}$ is the Raman intensity due to the polymer, and $C_{polymer}$ is the concentration (weight percent) of the polymer with respect to the complete formulation.

Several samples were prepared at a series of solute concentrations ranging from about 2 to about 16 wt % in approximately 2% intervals in an acrylate pressure sensitive adhesive matrix ($T_g \sim -10$ degrees C.). Linear concentration calibration curves were established for individual formulations based on the ratio of solute signal to polymer signal at characteristic peak positions.

Half of the samples were seeded with solute crystals, and the remaining formulations were left unseeded. Raman scans were performed on days 0, 2, 7 and 14 in seeded and/or unseeded samples showing solute crystallization. The concentration at the boundary of the crystal face and bulk formulation was determined for each time point. This can be completed, for example, by finding the minimum concentration on a plot of normalized intensity versus scan position, as in FIG. 9.

Figure 8:
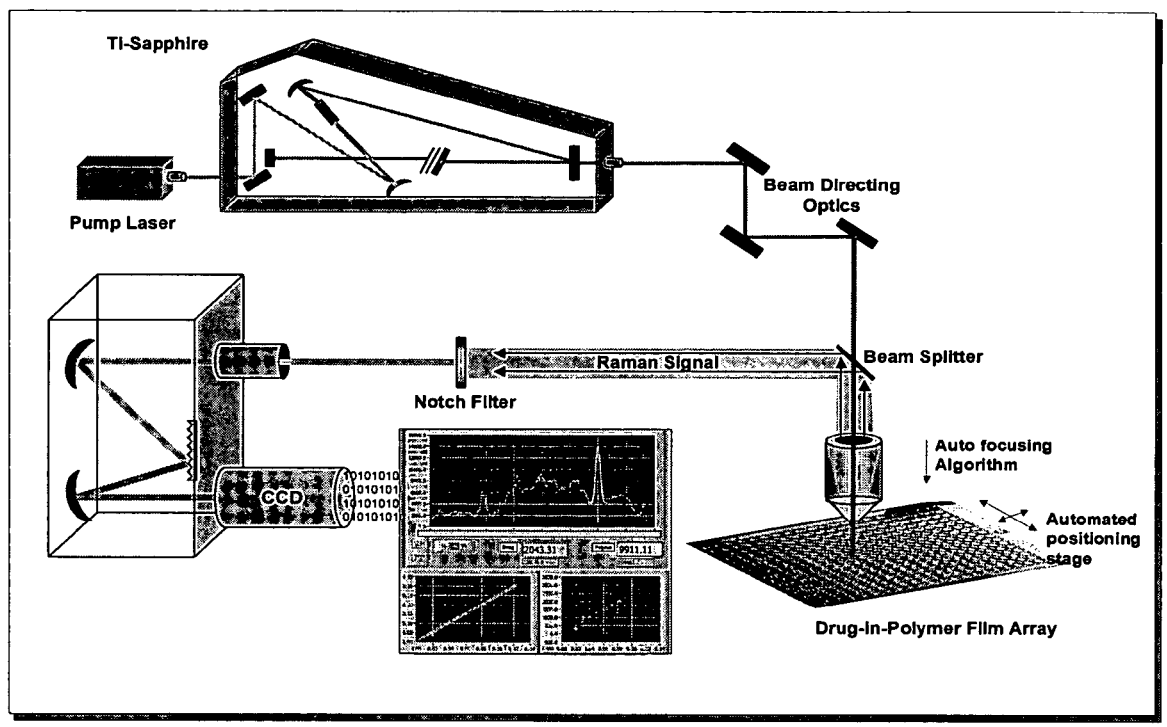
FIG. 8: One embodiment of an experimental setup for determination of $C_{sat}$ in polymer films

FIG. 8 shows an experimental setup for the determination of $C_{sat}$ of a solute in a polymer matrix or a polymer matrix film. A Ti:sapphire laser is tuned to an appropriate wavelength to measure the Raman scattering for a given solute. The beam is directed to one or more samples comprising polymer and solute. The Raman signal is collected, filtered from the background, and analyzed.

Figure 9:
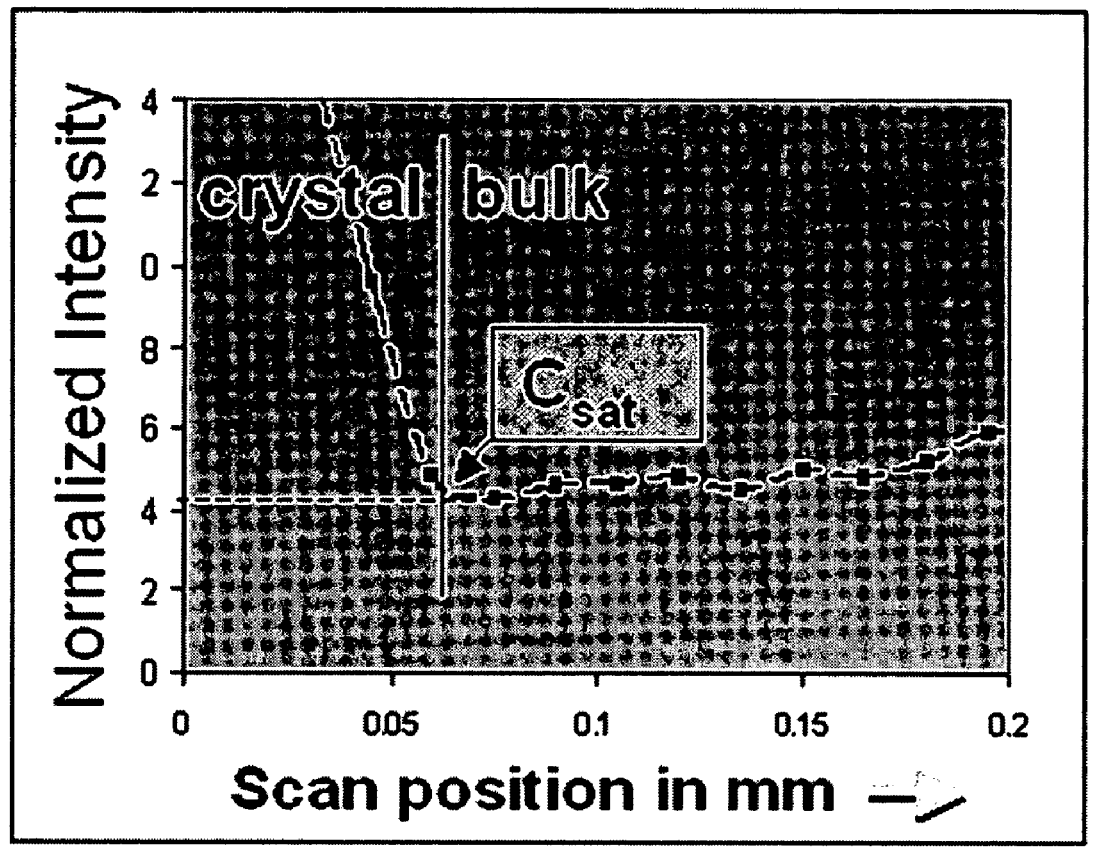
FIG. 9: Intensity vs. position plot depicting crystal interface
Figure 10:
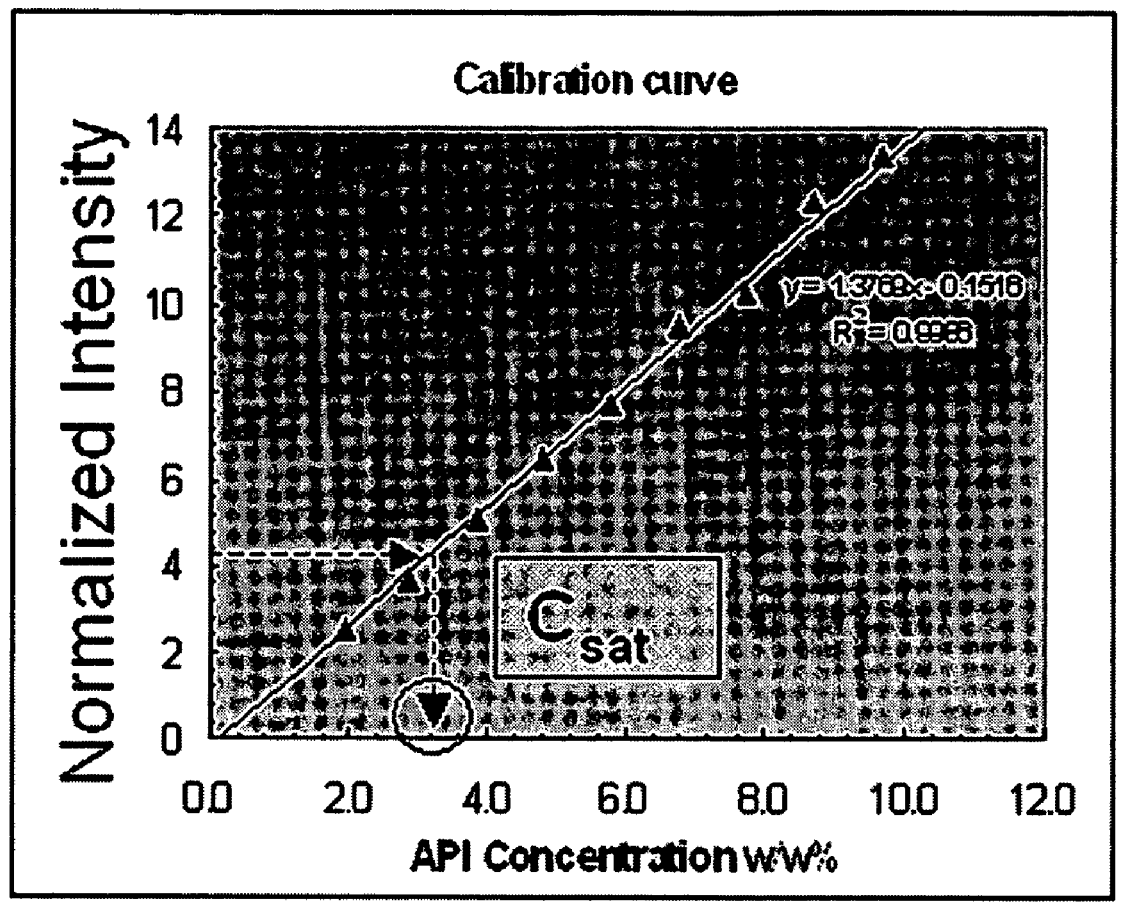
FIG. 10: Calibration curve for the determination of $C_{sat}$

FIG. 9 shows the Raman intensity due to both crystalline solute and solute in the bulk formulation. The saturation concentration is determined at the interface between the bulk material and the imbedded crystal. FIG. 10 shows a calibration curve of Raman intensity versus API concentration (percent weight). The $C_{sat}$ of a formulation can be determined from its normalized intensity.

Figure 11:
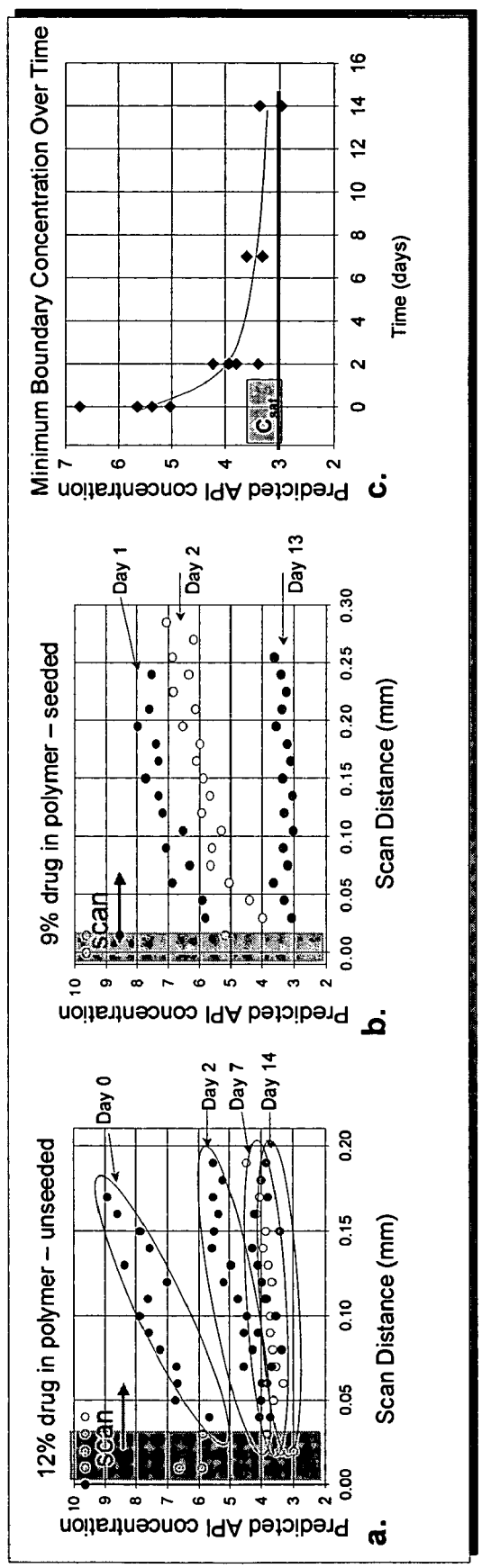
FIG. 11: Concentration profiles of two formulations and a plot of minimum boundary concentration

The API (drug) concentration profiles in FIG. 11 reflect an intermediate mechanism between pure diffusion limited crystallization and pure growth-limited crystallization. This is shown in FIG. 11 by both the decreasing slope of the concentration profiles beyond the boundary as a function of time and the decreasing minimum concentration over time. The left scheme of FIG. 11 (section a.) shows an unseeded formulation with 12% by weight solute (drug) in polymer. The center scheme of FIG. 11 (section b.) shows a seeded formulation with 9% by weight solute (drug) in polymer. In the right scheme of FIG. 11 (section c.), the minimum concentration asymptotically approaches the saturation concentration ($C_{sat}$).

Both the seeded and unseeded sample showed crystal growth in this experiment due to the high initial concentrations used. When the saturation concentration is not known, however, seeding can expedite the nucleation and growth of crystals and enable the interface to reach a state of equilibrium in samples above the saturation concentration. Both sample types consistently reached the same minimum boundary concentration over time (FIG. 11).

Overall, the formulation series visually observed at two weeks only showed crystals in samples higher than 5.7 weight %, and did not crystallize in samples with 4.0 weight % loading or lower. Using the present method, the median minimum boundary concentration was about 3.5 weight % at two days and about 3.0 weight % at 14 days.

What is claimed is:

1. A method of determining the saturation concentration of a solute in a polymer matrix or a polymer matrix film, comprising:
   (a) obtaining a calibration curve;
   (b) preparing samples with high solute concentration;
   (c) allowing said samples to reach equilibrium;
   (d) finding a crystal within said polymer matrix or polymer matrix film;
   (e) scanning a laser beam off the face of the crystal; and
   (f) determining $C_{sat}$ at the crystal interface.

2. The method of claim 1, wherein:
   (a) said calibration curve in step (a) comprises the intensity between the solute signal and the polymer matrix or polymer matrix film for each formulation;
   (b) said calibration curve in step (a) comprises the normalized intensity between the solute signal and the polymer matrix or polymer matrix film for each formulation;
   (c) said calibration curve in step (a) is constructed using several low solute level samples;
   (d) said samples in step (b) are prepared with high solute concentration and a high driving force to nucleate;
   (e) said samples in step (b) are prepared with seed crystals;
   (f) said crystal in step (d) is found using an in-line vision station;
   (g) said crystal in step (d) is found using a CCD camera;
   (h) said laser beam in step (e) is scanned in increments;
   (i) said laser beam in step (e) is scanned in increments of at least about 1.0 micrometer;
   (j) said laser beam in step (e) is scanned in increments of about 10.0 micrometers;
   (k) $C_{sat}$ is determined by analyzing a Raman signal at the interface; or
   (l) $C_{sat}$ is determined by analyzing a normalized Raman signal at the interface.

* * * * *